United States Patent [19]

Layton

[11] Patent Number: 5,365,777
[45] Date of Patent: Nov. 22, 1994

[54] RHEOMETER WITH FLOW DIVERTER TO ELIMINATE END EFFECTS

[75] Inventor: Ken S. Layton, Duncan, Okla.

[73] Assignee: Halliburton Company, Duncan, Okla.

[21] Appl. No.: 161,723

[22] Filed: Dec. 3, 1993

[51] Int. Cl.[5] .......................................... G01N 11/14
[52] U.S. Cl. ................... 73/54.28; 73/54.23; 73/54.37; 73/54.39; 73/54.33
[58] Field of Search .............. 73/54.28, 54.37, 54.21, 73/54.23, 54.33, 54.39, 54.37

[56] References Cited

U.S. PATENT DOCUMENTS

| | | | |
|---|---|---|---|
| 1,746,791 | 2/1930 | Osborne | 73/59 |
| 2,096,222 | 10/1937 | Bock | 265/11 |
| 2,354,923 | 8/1944 | McNamee | 73/59 |
| 2,382,979 | 8/1945 | Demp | 73/59 |
| 2,953,016 | 9/1960 | Seitz, Jr. | 73/60 |
| 3,111,838 | 11/1963 | Bucalo | 73/59 |
| 3,182,494 | 5/1965 | Beatty et al. | 73/59 |
| 3,269,171 | 8/1966 | Bruss et al. | 73/60 |
| 3,285,057 | 11/1966 | DeZurik | 73/59 |
| 3,292,423 | 12/1966 | Banks | 73/60 |
| 3,343,405 | 9/1967 | Gilinson et al. | 73/59 |
| 3,347,089 | 10/1967 | Perry | 73/59 |
| 3,435,666 | 4/1969 | Fann | 73/59 |
| 3,751,975 | 8/1973 | Katsura | 73/59 |
| 3,803,903 | 4/1974 | Lin | 73/59 |
| 4,175,425 | 11/1979 | Brookfield | 73/59 |
| 4,299,118 | 11/1981 | Gau et al. | 73/59 |
| 4,334,424 | 6/1982 | Kepes | 73/59 |
| 4,448,061 | 5/1984 | Brookfield | 73/59 |
| 4,566,324 | 1/1986 | Vinogradov et al. | 73/60 |
| 4,570,478 | 2/1986 | Soong | 73/60 |
| 4,571,988 | 2/1986 | Murphy, Jr. | 73/60 |
| 4,592,226 | 6/1986 | Weber et al. | 73/59 |
| 4,622,846 | 11/1986 | Moon, Jr. et al. | 73/59 |
| 4,668,911 | 5/1987 | Mueller et al. | 324/208 |
| 4,823,594 | 4/1989 | Gray | 73/54 |
| 5,167,143 | 12/1992 | Brookfield | 73/54.23 |

FOREIGN PATENT DOCUMENTS 672380 10/1963 Canada.

OTHER PUBLICATIONS

"TT100 In-Line Viscometer", Brookfield Engineering Laboratories, Inc.; Sep. 1988.
"TT200 Process Viscometer", Brookfield Engineering Laboratories, Inc.; Jun. 1990.

Primary Examiner—Hezron E. Williams
Assistant Examiner—David J. Wiggins
Attorney, Agent, or Firm—Stephen R. Christian; E. Harrison Gilbert, III

[57] ABSTRACT

A rheometer comprises a thin-walled bob having two ends, adjacent at least one of which ends there is disposed a respective flow diverter plate to eliminate adverse end effects caused by swirling fluid in the rheometer.

10 Claims, 2 Drawing Sheets

RHEOMETER WITH FLOW DIVERTER TO ELIMINATE END EFFECTS

BACKGROUND OF THE INVENTION

This invention relates to rheometers used for measuring fluid characteristics such as viscosity, which rheometers would but for the present invention tend to provide inaccurate measurements due to significant adverse end effects created by swirling fluid.

Various industries may need to test fluids to determine if they are suitable for their intended use. Fluid properties are often measured within pressurized environments. Fluid properties may be measured at elevated temperatures which may require pressure to prevent boiling. Certain fluids have a tendency to entrain air and fluid pressure is required to compress the air bubbles in the fluid. In real-time monitoring of processes, the fluid is continuously or semi-continuously pumped through the instrument at the process conditions.

Such fluids are often characterized as either Newtonian or non-Newtonian. To characterize a fluid as one of these, shear stress versus shear rate measurements are made. In Newtonian fluids, the shear stress versus shear rate is a constant called viscosity. Examples of Newtonian fluids are water and certain oils. In non-Newtonian fluids, the shear stress versus shear rate is not constant. Non-Newtonian fluids are classified by their shear stress versus shear rate curves as Power law, Bingham, or Pseudoplastic fluids. Examples of non-Newtonian fluids are gels, drilling muds, and cements. In non-Newtonian fluids, certain rheological properties or characteristics, such as $n'$, $K'$, yield stress, consistency, etc. are measured.

An apparatus used to measure shear stress versus shear rate is referred to herein as a rheometer, which term as used herein encompasses both multiple-speed testing and single-speed testing devices (the latter conventionally being referred to as a "viscometer" even if performed by the identical instrument capable of multiple-speed testing). In one embodiment, a rheometer is a couette type instrument in which a cup is turned at a constant speed or shear rate within a body of fluid contained in a chamber of a housing. A bob is suspended inside the cup. Fluid between the bob and cup imparts a torque or shear stress on the bob. This torque is measured and converted to the desired parameter viscosity) in a known manner. In an alternative embodiment, a paddle may be suspended inside the rotating cup. The resulting torque on the paddle can then be measured and converted to a fluid parameter (e.g., consistency).

In one such type of instrument, such as the Fann 35/50 series of rheometers, the sleeve of the rotating cup ends just after the bottom of the bob and the level of the fluid in the chamber does not extend much above the top of the bob. As a result, there is little swirl in the fluid at the respective ends of the bob. Because there is little swirl, the fluid imposes practically no effects on the ends of the bob to distort the measurement. Any such "end effects" which remain are essentially linear and can be readily compensated.

In a pressurized type of instrument, however, the entire system is full of fluid and in many such devices the bob is a thin walled tube because an extremely light part is needed. This common on devices such as the Brookfield TT-100 and the Brookfield TT-200. The combination of the device being filled with fluid along with the bob being basically a hollow tube makes the readings of this type of rheometer erratic and inconsistent. This because in this configuration the tested fluid undergoes moderate to very high swirl which creates moderate to very high non-linear end effects adversely affecting the rotation of the thin-walled type bob, thereby affecting the measurements that are responsive to such rotation. Thus, there is the need for an improved instrument of this type which does not undergo such adverse end effects and which thus provides consistent, accurate measurements.

SUMMARY OF THE INVENTION

The present invention overcomes the above-noted and other shortcomings of the prior art and meets the aforementioned need by providing a novel and improved rheometer which does not undergo adverse end effects. The invention combines a thin walled type of bob with fixed flow diverters to eliminate the adverse end effects. This results in readings that are free of the inconsistencies noted in other rotational rheometers. It is contemplated that this invention can be applied to all rotational rheological devices having end effect problems.

The rheometer of the present invention comprises a housing having a chamber defined therein for receiving a fluid. The rheometer also comprises a bob disposed in the chamber, which bob includes a side wall and an end member disposed at an end of the side wall. The side wall and end member define a cavity in the bob wherein the cavity is open at another end of the side wall opposite the end member. The rheometer further comprises a flow diverter plate suspended in the chamber adjacent one of the ends of the bob.

In the preferred embodiment, the rheometer still further comprises another flow diverter plate. This other flow diverter plate is suspended in the chamber adjacent the other end of the bob. Also included in the preferred embodiment is support means for suspending the flow diverter plates in the chamber, wherein the support means is connected to the housing and the flow diverter plates and passes through the bob.

Therefore, from the foregoing, it is a general object of the present invention to provide a novel and improved rheometer which does not undergo adverse end effects. Other and further objects, features and advantages of the present invention will be readily apparent to those skilled in the art when the following description of the preferred embodiment is read in conjunction with the accompanying drawings.

DETAILED DESCRIPTION OF PREFERRED EMBODIMENT

Figure 1:
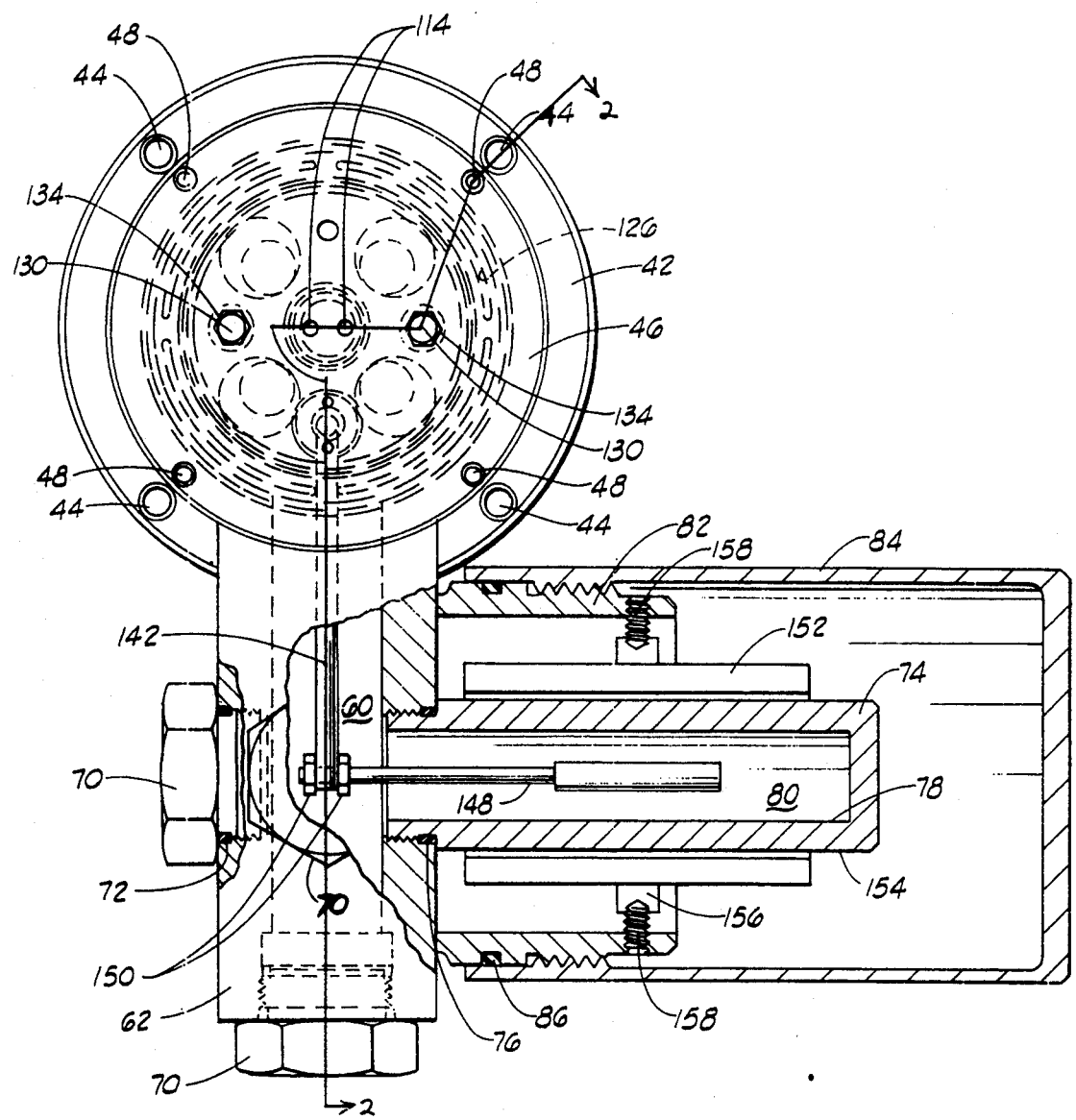
FIG. 1 is a partially sectioned end view of a rheometer containing the preferred embodiment of the present invention.

The present invention is implemented in its preferred embodiment as part of a rheometer wherein angular motion or torque of a bob is measured. The measured angular motion or torque is proportional to a rheological characteristic of a fluid in the rheometer. Various characteristics, such as consistency or cross-link time, can be measured in this way. In one use of the preferred embodiment described herein, viscosity is the measured characteristic and thus the rheometer could be called a viscometer; however, the broader term "rheometer" will be used. The preferred embodiment rheometer is shown in FIGS. 1 and 2.

Figure 2:
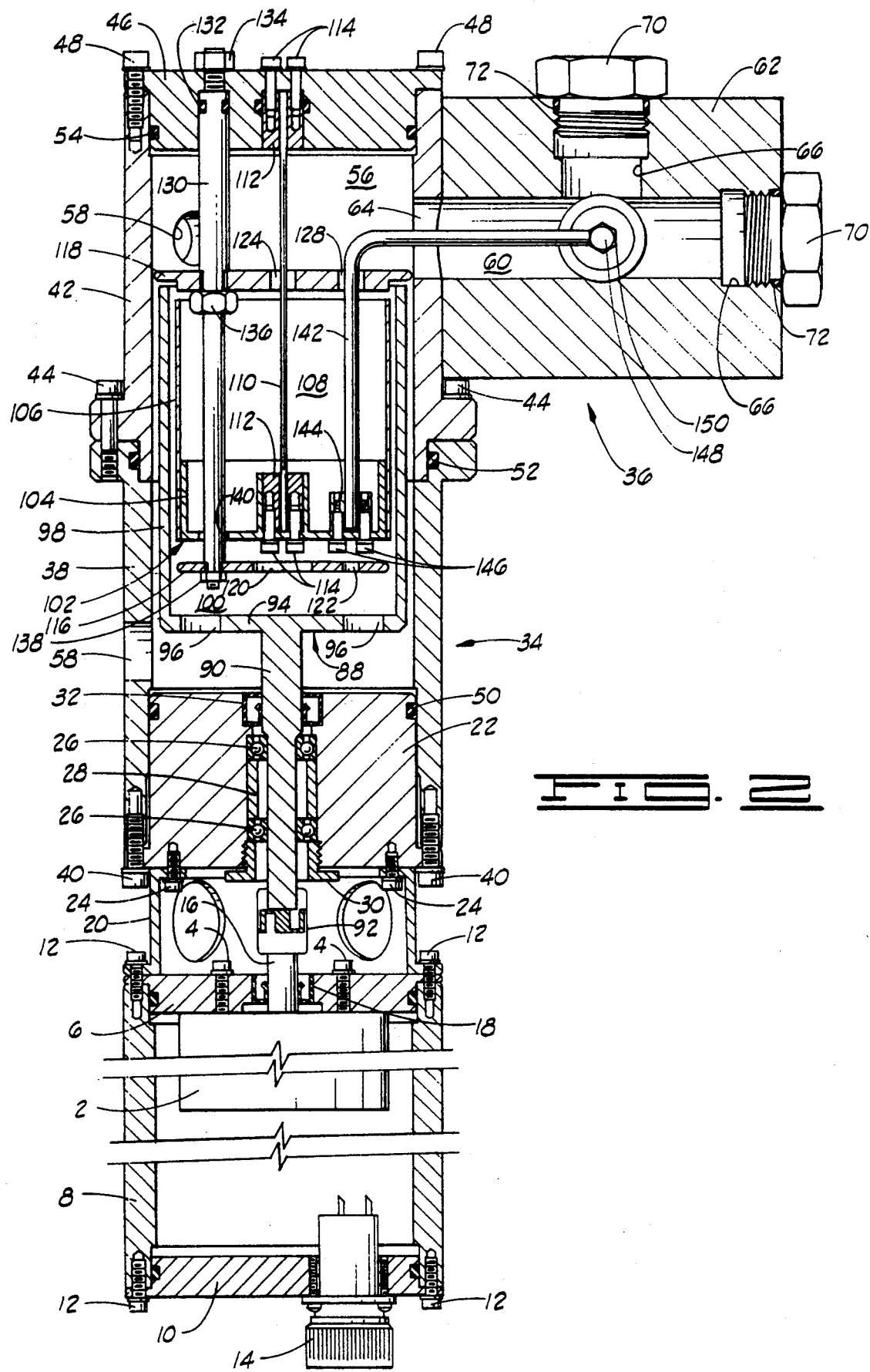
FIG. 2 is a sectional view of the rheometer taken along line 2—2 in FIG. 1.

Referring primarily to FIG. 2, the rheometer includes a motor 2, such as a DC servo motor, connected by screws and lock washers 4 to a motor mount 6 forming an end member of a motor housing also including a sleeve 8 and a cap member 10. These pieces are connected by screws and lock washers 12 as shown in FIG. 2. To get electrical signals to and from the motor 2, a connector 14 is mounted in the cap member 10 (the electrical connections are not shown but include two wires for the drive circuit to the motor and two wires for a tachometer circuit).

The rotor of the motor 2 rotates a drive shaft 16 which passes through a seal 18 mounted in the motor mount 6. The drive shaft 16 extends into a motor mount spacer 20 also connected to the motor housing by two of the screws and lock washers 12. The motor mount spacer 20 is connected to a bearing housing 22 by screws and lock washers 24. The bearing housing 22 carries ball bearings 26 separated by a bearing spacer 28 and secured in the bearing housing 22 by a bearing nut 30. The bearing housing 22 also carries a seal 32.

The bearing housing 22 forms an end member of the pressure housing of the rheometer. The pressure housing of the preferred embodiment comprises a main rheometer body 34 and a sensing means mounting body 36.

The main rheometer body 34 includes the aforementioned bearing housing 22 and a cylindrical sleeve 38 to which the bearing housing 22 is connected by screws and lock washers 40. The main rheometer body 34 also includes a cylindrical sleeve 42 connected by screws and lock washers 44 to the sleeve 38. A main body end member 46 also included in the main rheometer body 34 is connected by screws and lock washers 48 to the sleeve 42. These components are sealed by O-rings 50, 52, 54. A cylindrical compartment 56 is defined in the main rheometer body 34 by the inner surfaces of the facing bearing housing 22 and end member 46 and the inner surfaces of the sleeves 38, 42. Longitudinally spaced ports 58 defined in the sleeves 38, 42 provide for the communication of fluid under pressure with the compartment 56. The compartment 56 forms part of an overall chamber in the rheometer housing. This chamber also includes a compartment 60 defined in the sensing means mounting body 36.

The sensing means mounting body 36 includes an extension member 62 welded to the main body sleeve 42 so that a cylindrical channel of the compartment 60 defined in the extension member 62 communicates with the compartment 56 through a port 64 defined through the sleeve 42. Access ports 66 communicating with the compartment 60 are defined in the extension member 62 for a purpose to be described subsequently. As shown in the drawings, these ports 66 are closed by respective plugs 70 carrying respective O-rings 72.

Referring to FIG. 1, the sensing means mounting body 36 also includes a fluid isolation member 74 screwed into a threaded aperture of the extension member 62. This connection is fluid tightly sealed by an O-ring 76. The fluid isolation member 74 has an inner surface 78 defining a cylindrical channel 80 forming another part of the compartment 60 of the sensing means mounting body 36 and thus forming part of the overall chamber of the pressure housing of the rheometer.

Welded to the outer surface of the extension member 62 is an annular sub mount 82 (FIG. 1) to which a hollow cylindrical cover 84 is threadedly connected. An O-ring 86 provides a seal between the sub mount 82 and the cover 84.

The rheometer shown in the drawings also includes a member which is driven by the motor 2. Referring to FIG. 2, this member is particularly a rotatable cup 88 having a shaft 90 connected to the drive shaft 16 of the motor 2 by a flex coupling 92. The shaft 90 is an integral part of the cup 88 and extends from an end wall 94 which has openings 96 defined therein. Extending from the periphery of the end wall 94 opposite the shaft 90 end of the cup 88 to a free end of the cup 88 is a cylindrical side wall sleeve 98. This is a conventional rheometer cup of a type as known in the art, and it is rotated about the axis of the shaft 90 which is journaled in the ball bearings 26. A hollow region 100 is defined within the cup 88 by the inner surfaces of the end wall 94 and the side wall 98.

The rheometer further comprises reaction means for reacting to a characteristic of the fluid in the chamber of the rheometer. Specifically in the rheometer, the reaction means moves in the chamber in response to a rheological characteristic, namely viscosity, of the fluid which is typically pressurized in the chamber. In the preferred embodiment, the reaction means is embodied by a rotatable member 102 typically referred to as a bob. The bob 102 includes an end member or cap 104 and a cylindrical side wall sleeve 106. The sleeve 106 is connected to the cap 104 by a press fit and an adhesive such as epoxy. The end member 104 and the side wall 106 define in the bob 102 a cavity 108 which is open at the end of the side wall 106 opposite the end member 104.

The bob 102 is concentric within the rheometer cup 88 so that the end member 104 of the bob 102 is parallel to the end wall 94 of the cut 88 and so that the side walls thereof are parallel and concentric. In the preferred embodiment, the bob 102 is suspended in the hollow region 100 of the cup 88 by a flexible solid rod 110 connected at one end to the end member 46 of the main rheometer body 34 and at its other end to the end member 104 of the bob 102. These end connections are made by brazing (e.g., silver soldering) the rod 110 to respective metallic mounts 112 secured in their respective supports by screws and lock washers 114. The rod 110 defines the axis of rotation of the bob 102. As known in the art, such rotation preferably includes only limited angular motion about the axis of rotation (namely, a few degrees of rotation).

Still referring to FIG. 2, the rheometer of the preferred embodiment also includes two flow diverter plates 116, 118. The flow diverter plates 116, 118 eliminate swirling of the pressurized fluid adjacent the respective ends of the bob 102 and thereby eliminate adverse end effects. The flow diverter plate 116 is disposed within the hollow interior 100 of the cup 88 in between the end walls of the cup 88 and the bob 102. It is preferably adjacent but spaced from the end member 104 of the bob 102. The flow diverter plate 118 is adjacent but spaced from the open end of the bob 102 and the free end of the cup 88. The spacing of each of the flow diverter plates 116, 118 from its respective end of the bob 102 is preferably within the range of about 0.05 inch to about 0.50 inch. Each of the flow diverter plates 116, 118 of the preferred embodiment has a circular shape and is rigid.

The diameter of the flow diverter plate 116 of the preferred embodiment is approximately the diameter of the bob 102, which is slightly less (e.g., about 0.180 inch) than the diameter of the hollow region 100 of the cup 88. The flow diverter plate 116 has a central opening 120 and peripheral openings 122 which allow flow through the plate 116. The flow diverter plate 116 also includes two (one shown in the drawings) holes for receiving a support means for suspending the flow diverter plate in the chamber of the rheometer.

The diameter of the flow diverter plate 118 of the preferred embodiment is approximately the same as the outer diameter of the cup 88. The flow diverter plate 118 includes an axial opening 124 through which the rod 110 is disposed as shown in FIG. 2. The flow diverter plate 118 also includes slots 126 (FIG. 1) for permitting flow of the fluid through the diverter plate 118. A hole 128 is also provided for a purpose to be subsequently described. There are also two holes (only one shown in FIG. 2) through which the support means extends.

Such support means includes two elongated members defined in the preferred embodiment by straight rigid tie rods 130 (an end of each is shown in FIG. 1, but only one is shown in the section of FIG. 2). Each rigid rod 130 has one end rigidly connected to the end member 46 of the main rheometer body 34. This end is sealed by an O-ring 132 and secured by a nut 134. The support rod 130 extends through the respective opening in the flow diverter plate 118 and also through the respective aligned hole in the flow diverter plate 116 as shown in FIG. 2. The flow diverter plates 116, 118 are retained in respective fixed positions relative to the rod 130 by respective abutment shoulders of the rod 130 and respective retaining nuts 136, 138. It is to be noted that each support rod 130 also extends through a respective hole 140 defined through the end member 104 of the bob 102. Each rigid support rod 130 is disposed parallel to the flexible rod 110. The rods 130 fix the flow diverter plates 116, 118 in the spaced parallel relationship shown in the drawings. In the preferred embodiment, this relationship positions both of the flow diverter plates 116 118, as well as the interposed bob 102, between the fluid inlet/outlet ports 58 of the main rheometer body 34. This is preferred because the fluid is quickly forced through the sensing region. This gives an accurate length of time for the fluid to pass through the rheometer. Since this support means rigidly mounts the flow diverters to the housing, any amount of fluid swirl on either end of the bob 102 is eliminated.

The holes 140 in the end member 104 of the bob 102 are large enough to permit the needed small angular motion that can be imparted to the bob 102 in response to the rotational force of the cup 88 and the viscosity of the pressurized fluid in the radial annular space between the outer surface of the side wall 106 of the bob 102 and the inner surface of the side wall 98 of the cup 88. The holes 140, however, are small enough to engage the rods 130 if the bob 102 tends towards being over-rotated, such as otherwise could occur if material were to get stuck in the radial annular space between the cup 88 and the bob 102.

The rheometer of the preferred embodiment also includes sensing means for sensing the relatively limited angular motion of the bob 102. The sensing means specifically includes a linear variable differential transformer (LVDT) and a rigid linkage member 142. The linkage member 142 is an angle bar or rod, specifically one having a right angle bend in it in the preferred embodiment. One end of the member 142 is secured directly to the end member 104 of the bob 102 similarly to how the flexible rod 110 is connected thereto. This includes brazing an end of the linkage member 142 to a mount 144 that is held to the end member 104 by screws and lock washers 146. One leg of the illustrated linkage member 142 extends from this end connection through the interior cavity 108 of the bob 102 parallel to the flexible rod 110. This leg of the linkage member 142 passes through the hole 128 in the flow diverter plate 118, which hole 128 is large enough to allow for lateral movement of the linkage member 142. The other leg of the member 142 extends from the first mentioned leg through the opening 64 of the rheometer body sleeve 42 and into the compartment 60 of the sensing means mounting body 36. The end of this leg of the member 142 directly connects to a rod 148 of the LVDT. In the preferred embodiment, the rod 148 is positioned by the linkage member 142 four inches off the centerline or axis of the bob 102; this results in a significant displacement multiplication (i.e., the rod 148 moves farther than the bob 102, but in direct relation to the movement of the bob 102) so that the preferred embodiment has a measuring range of approximately 2000 to 1.

As more clearly shown in FIG. 1, the rod 148 is connected to the linkage member 142 by nuts 150. From this coupling, the rod 148 extends into the channel 80 of the fluid isolation member 74. As shown in FIG. 1, the rod 148 is wholly contained within the chamber of the rheometer (specifically the compartment 60 thereof). That is, there is no mechanical pass-through of the rod 148 or the linkage member 142 outside the walls defining the pressure chamber of the rheometer. Thus, the sensing means of the present invention does not require any seals or bearings for its implementation or use other than as necessary for defining the pressure chamber itself.

The rod 148 of the LVDT is rigidly linked to the bob 102 in a manner such that as the bob 102 rotates, the rod 148 is moved substantially linearly within the channel 80 of the fluid isolation body 74. That is, the linkage member 142 translates the rotational motion of the bob 102 to linear motion of the LVDT rod 148. Such linear movement of the rod 148 is detected by an electrical coil 152 of the LVDT disposed outside the fluid isolation member 74 (FIG. 1). In the preferred embodiment, the coil 152 is connected adjacent and concentrically about an outer surface 154 of the fluid isolation member 74 by a clamp mount 156 and set screws 158 supported by the sub mount 82. The electrical coil 152 provides an electrical characteristic (namely, inductance) which is responsive to movement of the rod 148 so that an electrical signal generated in response to the electrical characteristic represents torque of the bob 102. Such relationship is known in the art. In particular, the coil 152 can be connected as part of a known oscillator circuit wherein the generated oscillating signal has a frequency which is responsive to the inductance of the coil 152 (which inductance is responsive to the position of the rod 148) and which can be converted to torque of the bob 102 knowing the particular construction of the bob 102, the rotational velocity and the flexural characteristics of the rod 110 by which the bob 102 is suspended in the chamber of the rheometer. To so use the LVDT in a proper manner, it first needs to be calibrated. This can be done by adjusting the initial position of the rod 148 in the channel 80 through the access ports 66 in the sensing means mounting body 36.

The torsional bending of the rod 110 is linear with respect to the torque; therefore, the signal produced by the LVDT is linear with respect to the viscosity. As the torque increases, there is a direct linear change in the voltage output of the LVDT.

Because the LVDT sensing mechanism of the present invention does not require seals or bearings, it can be used with any fluid and at any pressure which the structural elements can withstand. Accordingly, the materials of construction are of types known in the art suitable for use with the particular fluids, temperatures and pressures to be used.

A torque measuring method can be performed using the rheometer described above. This method comprises providing a fluid (typically a pressurized and/or heated fluid) in the chamber defined in the housing. Such fluid is provided to the compartments 56, 60 defining the chamber by flowing the fluid through one or more of the ports 58 defined in the main rheometer body 34.

The torque measuring method also comprises creating a reactive motion in the chamber in response to a characteristic of the pressurized fluid. Using the described rheometer, creating a reactive motion includes rotating the cup 88 in the chamber provided with the pressurized fluid so that the bob 102 disposed in the chamber within the cup 88 angularly moves in response to viscosity of fluid between the cup 88 and the bob 102.

The method further comprises moving the rod 148 of the linear variable differential transformer in response to the reactive motion, wherein the rod 148 is disposed and moved in the pressurized fluid in the chamber. In the described embodiment, moving the rod 148 includes rigidly linking the bob 102 and the rod 148 within the chamber so that both the bob 102 and the rod 148 move within the pressurized fluid in response to viscosity of the fluid between the cup 88 and the bob 102.

The method still further comprises sensing movement of the rod 148 and generating outside the chamber an electrical signal in response to the sensed movement, wherein the electrical signal represents torque. This is performed in the preferred embodiment as described above (e.g., using an oscillator circuit and known numerical conversion techniques).

Thus, the present invention is well adapted to carry out the objects and attain the ends and advantages mentioned above as well as those inherent therein. While the preferred embodiment of the invention has been described for the purpose of this disclosures changes in the construction and arrangement of parts and the performance of steps can be made by those skilled in the art, which changes are encompassed within the spirit of this invention as defined by the appended claims.

What is claimed is:

1. A rheometer, comprising:
   a housing having a chamber defined therein for receiving a fluid;
   a bob disposed in said chamber, said bob including a side wall and an end member disposed at an end of said side wall, said side wall and end member defining a cavity in said bob wherein said cavity is open at another end of said side wall opposite said end member; and
   a flow diverter plate fixedly suspended in said chamber adjacent one of said ends of said bob.

2. A rheometer as defined in claim 1, further comprising another flow diverter plate, said another flow diverter plate suspended in said chamber adjacent the other of said ends of said bob.

3. A rheometer as defined in claim 2, further comprising support means for suspending said flow diverter plates in said chamber, said support means connected to said housing and said flow diverter plates and passing through said bob.

4. A rheometer as defined in claim 3, wherein:
   said bob is disposed in said chamber so that said bob is rotatable about an axis; and
   said support means includes an elongated member connected at an end thereof to said housing and connected at another end thereof to one of said flow diverter plates and intermediate said ends thereof connected to the other of said flow diverter plates and disposed through said bob parallel to said axis.

5. A rheometer as defined in claim 2, further comprising a rotatable cup disposed in said chamber of said housing, said cup having a hollow region defined therein between a shaft end of said cup and a free end of said cup, and wherein said bob and one of said flow diverter plates are disposed in said hollow region and wherein the other of said flow diverter plates is disposed adjacent said free end of said cup.

6. A rheometer, comprising:
   a housing having a chamber defined therein for receiving a fluid under pressure;
   a cup including a shaft, a cup end wall connected to said shaft and a cylindrical cup side wall connected to said cup end wall, wherein said cup is mounted in said housing so that said cup end wall and said cup side wall can be rotated in said chamber;
   a motor connected to said housing and said shaft of said cup for rotating said cup;
   a bob including a bob end member and a cylindrical bob side wall connected to said bob end member, said bob disposed in said cup so that said bob end member is parallel to said cup end wall and so that said bob side wall is concentric with said cup side wall;
   a first flow diverter member, said first flow diverter member disposed fixedly in said cup between said cup end wall and said bob end member for eliminating adverse end effects of fluid under pressure adjacent said bob end member;
   a second flow diverter member, said second flow diverter member disposed fixedly in said chamber of said housing adjacent an end of said bob side wall and an end of said cup side wall opposite said bob end member and said cup end wall for eliminating adverse end effects of fluid under pressure adjacent said end of said bob side wall opposite said bob end member;
   means for connecting said bob to said housing so that said bob can rotate relative to said housing; and
   means for connecting said first and second flow diverter members to said housing.

7. A rheometer as defined in claim 6, wherein:
   said means for connecting said bob includes a flexible rod passing through said second flow diverter member and having an end connected to an end of said housing and having another end connected to said bob end member; and
   said means for connecting said first and second flow diverter members includes a rigid rod connected to said end of said housing and to said first and second flow diverter members, said rigid rod passing through said bob end member.

8. A rheometer as defined in claim 7, wherein:

said flexible rod defines an axis of rotation for said bob relative to said housing; and said rigid rod extends parallel to said flexible rod.

9. A rheometer as defined in claim 8, wherein:

said housing includes spaced fluid ports through which the fluid under pressure is communicated with said chamber of said housing; and said bob and said first and second flow diverter members are disposed between said fluid ports.

10. A rheometer as defined in claim 6, wherein:

said housing includes spaced fluid ports through which the fluid under pressure is communicated with said chamber of said housing; and said bob and said first and second flow diverter members are disposed between said fluid ports.

* * * * *